(12) United States Patent
Haller et al.

(10) Patent No.: US 8,371,496 B2
(45) Date of Patent: Feb. 12, 2013

(54) METHOD AND APPARATUS FOR TREATING GLASS BODIES, AS WELL AS A GLASS BODY AND MEASURING PROBE

(75) Inventors: Wolfgang Haller, Chevy Chase, MD (US); Othmar Hayoz, Urdorf (CH); David Merino, Zurich (CH); Thomas Allenspach, Besenbueren (CH)

(73) Assignee: Mettler-Toledo AG, Griefensee (CH)

( * ) Notice: Subject to any disclaimer, the term of this patent is extended or adjusted under 35 U.S.C. 154(b) by 1320 days.

(21) Appl. No.: 11/162,960

(22) Filed: Sep. 29, 2005

(65) Prior Publication Data
US 2006/0096975 A1 May 11, 2006

Related U.S. Application Data

(63) Continuation of application No. PCT/EP2004/050407, filed on Apr. 1, 2004.

(30) Foreign Application Priority Data

Apr. 2, 2003 (DE) .................................. 103 15 161

(51) Int. Cl.
*B23K 31/02* (2006.01)
(52) U.S. Cl. ...................... 228/121; 228/245; 228/248.1
(58) Field of Classification Search .................. 228/121, 228/126, 131, 102, 103, 132, 245, 248.1, 228/249, 6.1, 8, 9, 133, 8.9; 204/420
See application file for complete search history.

(56) References Cited

U.S. PATENT DOCUMENTS

| 1,936,231 | A | * | 11/1933 | Gelstharp et al. ............... 501/70 |
| 3,445,256 | A | | 5/1969 | Dalton |
| 3,523,777 | A | | 8/1970 | Petersen |
| 3,607,171 | A | * | 9/1971 | Hirsch .............................. 65/22 |
| 3,855,095 | A | | 12/1974 | Leonard |
| 4,107,979 | A | * | 8/1978 | Saeda et al. ..................... 73/785 |
| 4,661,236 | A | | 4/1987 | Gelo |
| 4,687,500 | A | | 8/1987 | Gelo |
| 5,223,123 | A | | 6/1993 | Koch |
| 5,316,649 | A | | 5/1994 | Kronberg |

(Continued)

FOREIGN PATENT DOCUMENTS

| DE | 19541241 A1 * | 5/1997 |
| JP | 02-208232 | 8/1990 |

OTHER PUBLICATIONS

Mortimer, Charles Das Basiswissen der Chemie , Georg Thieme Verlag, Stuttgart 1987 pp. 335-339.

(Continued)

*Primary Examiner* — Maria Veronica Ewald
*Assistant Examiner* — Megha Mehta
(74) *Attorney, Agent, or Firm* — Standley Law Group LLP

(57) ABSTRACT

The method and apparatus serve to treat a multi-walled glass body, in particular a glass body (20) with a glass membrane (25) for a chemical sensor or measuring probe, wherein a portion of at least one wall or of an interior tube (21) is to be fused, and wherein the fusing can have the purpose of closing off a first chamber (291). A glass element (286) which serves to absorb radiation energy is inserted in the vicinity of the portion (210) of either the wall or of the interior tube (21) that is to be fused. The glass element (286) is exposed to the radiation energy of at least one energy radiator (17), whereby the glass element (286) and the portion (210) of either the wall or the interior tube (21) are fused together.

12 Claims, 5 Drawing Sheets

U.S. PATENT DOCUMENTS

| | | | |
|---|---|---|---|
| 6,033,543 A * | 3/2000 | Zeidler | 204/420 |
| 6,354,901 B1 | 3/2002 | Bundo | |
| 6,442,978 B1 * | 9/2002 | Kamio et al. | 65/488 |
| 6,641,449 B2 | 11/2003 | Johnston | |

OTHER PUBLICATIONS

Mettler-Toledo GMBH, "Low-maintenance pH electrodes and systems: Reduce your overall process costs!", Aug. 2001, 8 pages, Urdorf, Switzerland.

Mettler-Toledo GMBH, "InPro 2000 liquid-electrolyte pH electrodes with integrated temperature sensor.", Jan. 2002, 2 pages, Urdorf, Switzerland.

Mettler-Toledo GMBH, "InPro 3200(SG) gel-electrolyte pH electrodes with integrated temperature sensor.", Jan. 2002, 2 pages, Urdorf, Switzerland.

Mettler-Toledo GMBH, "Wartungsarme pH-Elektroden und pH-Systeme: So reduzieren Sie Ihre Prozesskosten.", Sep. 2002, 6 pages, Urdorf, Switzerland.

Mettler-Toledo GMBH, "InPro 2000 pH-Elektroden mit Fluessigelektrolyt und integriertem Temperaturfuehler.", Oct. 2000, 2 pages, Urdorf, Switzerland.

Mettler-Toledo GMBH, "InPro 3200(SG) pH-Elektroden mit Gelelektrolyt und integriertem Temperaturfuehler.", Jan. 2002, 2 pages, Urdorf, Switzerland.

* cited by examiner

FIG 4
FIG 5
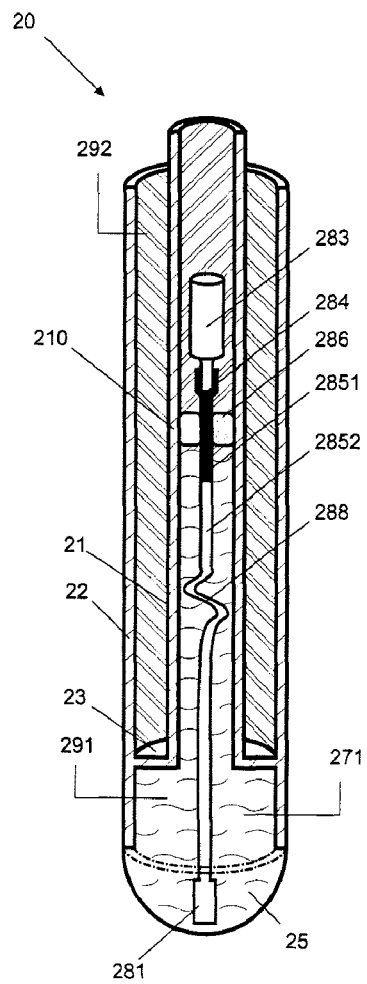
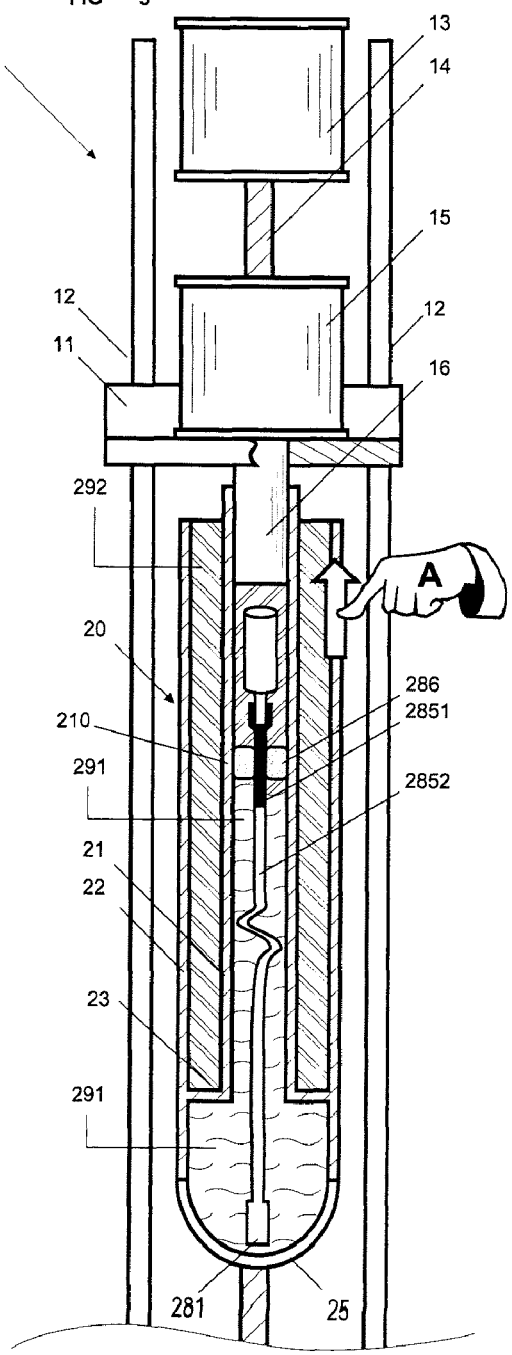

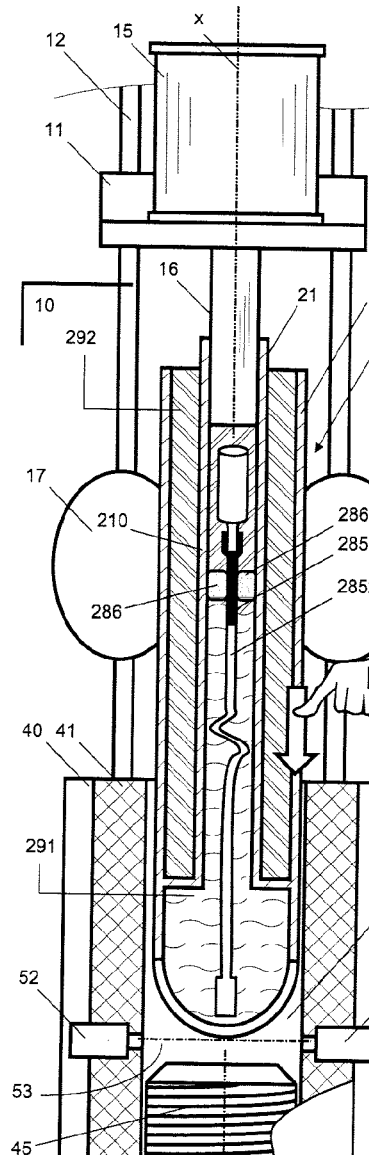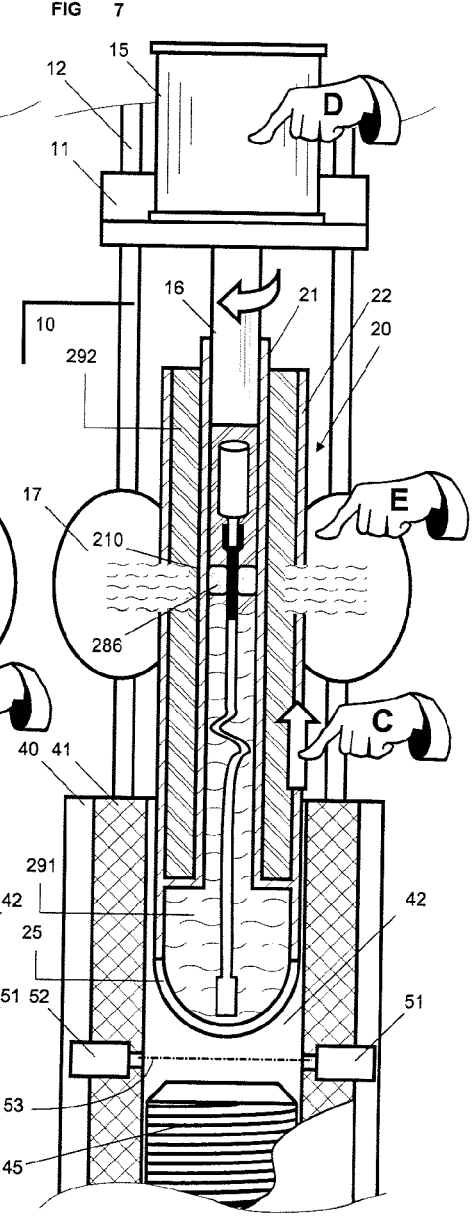

METHOD AND APPARATUS FOR TREATING GLASS BODIES, AS WELL AS A GLASS BODY AND MEASURING PROBE

CROSS-REFERENCE TO PENDING APPLICATIONS

The present invention is a continuation of, and claims benefit of domestic priority from, PCT application PCT/EP2004/50407, filed 1 Apr. 2004, which designates the United States and which in turn claims benefit of foreign priority from German application 10315161.3, filed 2 Apr. 2003. The PCT application is incorporated by reference as if fully recited herein.

TECHNICAL FIELD

The invention relates to a method and an apparatus for treating multi-walled glass bodies, and it further relates to a glass body and to a measuring probe that is equipped with the glass body as described in the appended claims.

BACKGROUND OF THE ART

The invention relates in particular to a method and apparatus for treating glass bodies that are equipped with measuring components and are used for chemical sensors, in particular pH electrodes of the kind described, e.g., in the following product sheets of Mettler-Toledo GmbH, CH-8902 Urdorf, Switzerland: "Low-maintenance pH electrodes and systems", September 2002; "InPro 2000 pH-Elektroden mit Flüssigelektrolyt und integriertem Temperaturfühler" (*InPro 2000 pH electrodes with fluid electrolyte and integrated temperature sensor*), October 2000; or "InPro 3200 (SG) pH-Elektroden mit Gelelektrolyt und integriertem Temperaturfühler" (*InPro 2000 pH electrodes with gel electrolyte and integrated temperature sensor*), January 2002.

The principal arrangement of the pH electrodes, which are configured as combination electrodes and include a glass electrode and a reference electrode, is presented in the above-cited references, as well as in the attached FIG. 1. Under the design concept of the combination electrode, the glass electrode which has a lead-off element 281 and the reference electrode which has a reference element 282 are built as a combined unit. The reference electrode surrounds the glass electrode like a ring. The functional principle of these pH electrodes is described in Charles E. Mortimer, "Chemie, Das Basiswissen der Chemie", 5. Auflage, Georg Thieme Verlag, New York 1987, pages 337-338, with reference to Figure 20.9 which illustrates an experimental setup.

Inside a first chamber 291, which is enclosed in an interior tube 21 and terminates in a thin-walled glass hemisphere or glass membrane 25, the lead-off element 281, which normally consists of silver/silver chloride, is immersed in a solution of defined pH value or in an inner buffer 271 representing the electrically conductive connection between the inside surface of the glass membrane 25 and the lead-off element 281 (concerning buffer see Mortimer, page 292).

The semi-permeable glass membrane 25 is pH-sensitive. An electrical potential, which occurs across the semi-permeable glass membrane 25 represents a direct measure for the pH value of the tested solution or other substance to be measured. As soon as the pH electrode is dipped into the substance to be measured, the glass membrane 25 begins to swell on the outward-facing side, as sodium ions $Na^+$ are replaced by hydrogen ions $H^+$. The inside is always in a swollen state as it is permanently wetted by the inner buffer 271. The pH value of the inner buffer is normally set at pH7, i.e., at the neutral level. The swollen surface layers, which have a depth of less than 0.0001 mm, can absorb the hydrogen ions of the solution and the ions of the inner buffer by diffusion. If the pH electrode is immersed in a test substance with the same concentration of protons as the inner buffer 271, the difference between the respective electric charges of the inner buffer and the test substance is ideally equal to zero. Consequently, no electrical potential occurs in this case across the glass membrane 25. From the absence of an electrical potential, one can derive the conclusion that the test substance has likewise a pH value of 7. If the test substance has more or fewer positive charges than the inner buffer 271, there will be a difference in the electrical potential, where the polarity of the difference indicates whether the test substance has a surplus or deficit of positive charges.

The voltage potential that occurs in the lead-off element 281 is compared to the voltage potential that establishes itself at the reference element 282. Under idealized assumptions, the voltage potential at the reference element 282 remains constant, independent of the ion concentration in the test substance. The difference between the two voltage potentials forms the actual measuring signal which provides information about the ion concentration in the test substance.

The reference element is immersed in an electrolyte, normally a potassium chloride (KCl) solution 272, and conductively connected to the latter through ion migration. The KCl solution 272, which is enclosed inside a second chamber 292 between the outside wall of the interior tube 21 and the inside wall of the exterior tube 22 diffuses slowly through a porous separating wall or diaphragm 26 into the test substance and thereby establishes the electrical connection to the latter. It is important for the diaphragm 26 to be fluid-permeable for the KCl solution 272, but on the other hand, the test substance cannot be allowed to migrate from the outside into the KCl solution 272. This can be prevented for example by always keeping the top surface of the KCl solution 272 at a higher level than the top surface of the test substance. Furthermore, the outward diffusion of the KCl solution should be as strong as possible in order to keep the internal electrical resistance small. Thus, the diaphragm 26 is a porous separator between the KCl solution 272 and the test substance, which normally has a different ion concentration. The diaphragm 26 prevents the solutions on the one hand from equalizing their levels of ion concentration, while on the other hand an ion stream flows through the diaphragm.

The glass membrane 25 consists of a special glass with a thickness of for example 0.3 to 0.5 mm, which is preferably blown into a hemispherical shape to optimize its mechanical stability. The composition of the glass is for example 72% $SiO_2$, 22% $Na_2O$, and 6% $CaO$, which can be obtained by melting corresponding quantities of $SiO_2$, $Na_2CO_3$ and $CaCO_3$.

The preferred way of producing the glass body of the pH electrode is to use an immersion tube 2 which, as shown in FIG. 2a, has an exterior tube 22 whose inside wall is connected to the interior tube 21 by means of a ring plate 23 so as to form a first chamber 291 which is to be closed off on one side by the glass membrane 25, and a second chamber 292 which is closed off on one side by the ring plate 23.

To form the glass membrane 25, the immersion tube 2 is introduced into a crucible containing molten glass and a small quantity of the molten glass, a so-called gob 24 is taken out which attaches itself to the lower rim of the exterior tube 22, as shown in FIG. 2b. Through an in-flow of a gaseous medium, the molten glass gob 24 can be blown into a thin-walled hemispherical glass membrane 25, whereby the glass body 20 shown in FIG. 2c is produced.

FIG. 3a shows the glass body 20 of FIG. 2c with the first chamber 291 filled with an inner buffer 271 and with a lead-off element 281 installed. The lead-off element 281 has a terminal wire 285 which is connected, preferably by means of a press-clamped connection 284, to a plug contact 283 which serves to connect the measuring instrument. Of course, there are other ways to connect the terminal wire 285 to the measuring instrument. For example, a connecting portion of the terminal wire 285 can be taken to the outside of the glass body 20 and electrically contacted, e.g., by soldering.

To separate the first chamber 291 and the second chamber 292 from each other, it is preferred to seal the first chamber 291 tightly after the chamber 291 has been filled with the inner buffer 271 and the lead-off element 281 has been installed. Among other things, this serves to avoid contamination of the inner buffer 271, for example when contacting the plug connector 283.

Under the prior art concept, which is illustrated in FIG. 3b, a part 220 of the exterior tube 22 was removed in order to expose the interior tube 21, so that a portion 210 of the interior tube could be heated by means of a burner and fused together. Thus, the first chamber 291 is closed off by the fused portion 210 of the interior tube 21, whereby the inner buffer 271 is prevented from leaking out, and foreign substances are prevented from entering.

After the interior tube has been fused, the separated portions of the exterior tube 22 need to be joined again. The rejoined portions need to be in precise coaxial alignment so that, e.g., a pH electrode equipped with the finished glass body 20 can be installed with a precise fit in an appropriate receptacle, for example in an armature.

However, the foregoing prior-art method of producing glass bodies and, more specifically, of fusing an interior tube of a glass body containing measuring components, can only be performed by experienced personnel at considerable expense.

A method and apparatus for producing a fluid electrode with an interior tube and an exterior tube are described in U.S. Pat. No. 4,661,236 to Gelo ("Gelo '236"), wherein the interior tube is filled with a solution in which a metal contact is immersed. The metal contact passes from the interior tube through a hermetically sealed closure which separates the fluid from the surrounding space. The method is distinguished by the fact that the interior tube consists of a glass that absorbs electromagnetic waves of selected wavelengths, while the exterior tube is transparent for the same wavelengths with almost no absorption. To produce the hermetic closure, the interior tube is fused shut through irradiation at an appropriately selected wavelength, so that the tube melts and contracts itself around the metal contact.

The foregoing method can pose a problem that occurs in a process step prior to the fusing of the interior tube, specifically in the step of forming the membrane, in that the heat which is radiated from the molten glass in the crucible is absorbed by the material of the interior tube, whereby the connection between the interior tube and the exterior tube, e.g., by way of the aforementioned ring plate, can come loose. According to Gelo '236, this problem can be solved by using two different types of glass for the interior tube, where the lower portion of the interior tube is made of the same type of glass as the exterior tube, and the upper portion of the interior tube is made of the type of glass that absorbs the electromagnetic waves.

This kind of tube, which is made of two types of glass, is relatively expensive to produce. Moreover there is a risk, when the tube contracts in the melting region, in that the closure between the wall of the tube and the metal contact will occur not to be complete. Therefore the described method of fusing needs a length of time that is exactly scheduled. Furthermore, controlling the exact position of the fusion of the interior tube requires a complex optical adjustment in order to focus the radiation on the right spot.

U.S. Pat. No. 3,855,095 to Leonard discloses an electrode having an interior tube and an exterior tube both made of glass, wherein the interior glass tube is fuse-melted by means of a glass element. The fuse-melting process occurs by means of inductive heating, wherein a tool is used for the coupling of the heat to the glass element. The application of means to produce sonic energy is proposed as well.

The present invention therefore has the objective to provide an improved process and an improved apparatus for treating multi-walled glass bodies, further to provide a glass body that is produced in accordance with the improved method, as well as a measuring probe that is equipped with the glass body.

In particular, the invention aims to provide an improved method of treating multi-walled glass bodies, wherein the method offers an inexpensive way in which chambers inside a glass body can be tightly closed off.

As a further objective, the invention aims to provide an apparatus that is inexpensive to build and easy to operate, whereby glass bodies can be finished rapidly and precisely, preferably through an automated process.

SUMMARY OF THE INVENTION

The foregoing objective is met by providing a method, an apparatus, a glass body, and a measuring probe with the features described and claimed in the appended claims. Advantageous further developed embodiments of the invention are presented in dependent claims.

The inventive method and apparatus serve to perform certain steps in the process of treating a multi-walled glass body, in particular a glass body of the kind that has a glass membrane and is used in a chemical sensor or measuring probe, wherein at least one wall or an interior tube of the glass body is to be partially fused, including the case where a first chamber is to be closed off by the fusion.

According to the invention, a glass element in solid or powder form that serves to absorb radiation energy is inserted in the area of the wall portion or interior tube portion that is to be fused. The glass element is irradiated by at least one source of radiation energy in such a manner that the glass element is fused together with the wall portion or interior tube portion, wherein the fuse-melting step is controlled by a displacement of part of the wall or the interior tube, that adjoins to a soft melting zone, relative to the exterior tube.

The fusion-melting liquefies and deforms the glass element, so that the glass element makes surface contact with and thereby melts the adjacent portion of the interior tube or wall, whereby the glass element and the interior tube or wall are fused together. Since the glass element does not need to be in solid contact with the adjacent interior tube portion before the irradiation is started, the glass element can be inserted and correctly positioned in the glass body without a problem.

The foregoing method is particularly advantageous for fusing interior tubes of glass bodies that are used in pH electrodes. This type of glass body has a first chamber inside an interior tube, which is filled with an inner buffer and closed at one end by a glass membrane. Under the inventive method, the first chamber is tightly sealed by fusing a part of the interior tube. The exterior tube is left in one piece during the fusion process.

An electrically conductive terminal lead that does not melt in the process and the at least one glass element are inserted together into the interior tube. The terminal lead passes through the part of the interior tube that is to be fused and forms the connection between a lead-off element which is immersed in the inner buffer and a connector plug on the outside of the first chamber. The terminal lead consists preferably of a precious metal, for example platinum, which does not melt during the process steps that are performed on the glass body.

Preferably, the non-melting electrically conductive terminal lead is surrounded by a ring-shaped glass element in order to facilitate the correct positioning of the latter.

Under a preferred concept of the invention, the glass element which serves to absorb the radiation energy contains metal oxides or metals that are present in monolithic form or in more than one piece, or in particle form. The metal oxides or metals are heated by exposure to radiation energy, for example infrared radiation, or by inductive energy-coupling.

Glass bodies containing an energy-absorbing glass element can thus be processed without the need to cut away parts of the exterior tube.

In the proposed method, it is essential to have precise control over the fusion process and the forces that act on the parts adjacent to the fusion zone. It needs to be prevented, for example, that the interior tube is separated in two or that other parts of the glass body are harmed. It also needs to be prevented that parts which remain only loosely connected during the fusion process are twisted relative to each other, which may be detrimental to the desired functionality or the appearance of the glass body.

To solve the foregoing problem, the glass body part that is to be subjected to the fusion process, for example the interior tube, is held in a fixed position in such a manner that the part which during the fusion process is connected to the fixed part only through the melted material can move only in the axial direction, i.e., along the longitudinal axis of the interior tube. Thus, all parts of the glass body remain in axial alignment. The inventive concept further includes a means of limiting the movement of the free portion of the interior tube to a desired amount, for example with a limit stop.

The inventive concept also includes a guide arrangement to precisely guide the glass body along a prescribed axis during the fusion process.

The glass element that serves to absorb the radiation energy is preferably heated uniformly, so that the surrounding interior tube is contacted uniformly after the glass element has been brought into the liquid phase. This is accomplished preferably by attaching the interior tube to the shaft of a motor that spins the glass body during the fusion process. The forces that are generated by the rotation ideally have the effect that the molten material of the glass element is pressed against the interior tube along a ring-shaped contact area, so that the contacted portion is evenly heated.

The displacement of the parts of the immersion tube that are free to move during the fusion process is used advantageously to detect the phase change in the portion of the interior tube that is to be fused and to control the energy radiator in such a manner that the glass body, and specifically the interior tube, is exposed to no more than the required amount of energy. Preferably, the arrangement includes an optical sensor, for example a light gate or a camera, which detects the displacement of the free part of the interior tube and sends a signal to a control unit. It is also possible to use sensors operating on other, non-optical principles, for example capacitive sensors.

The same light gate can further be used as a reference line for the positioning of the glass body. For example, the glass body is lowered to the reference line and subsequently raised by a fixed amount, so that it is correctly positioned in the working zone of the energy radiators.

The light gate is preferably positioned in such a manner that it can be used as reference line before the fusion-melting process and as a detection line during the fusion-melting process. Of course, one could also use more than one light gate.

The apparatus according to the invention is therefore preferably equipped with a stage that slides on a track and is driven and controlled by a motor, so that the glass body can be fastened to the stage and moved into the working range where the radiation energy emitted by at least one energy radiator can interact with the glass element that has been inserted into the glass body. Thus, the method according to the invention can be performed in a convenient and largely automated manner with an apparatus of simple construction.

BRIEF DESCRIPTION OF THE DRAWINGS

The invention will be further explained hereinafter with reference to drawings, wherein identical parts are identified with identical reference numerals and wherein:

FIG. 4 is the glass body 20 of FIG. 2c, where the first chamber 291 has been filled with the inner buffer 271 by way of the slightly lengthened interior tube 21, and where the lead-off element 281 has been installed, centered by means of an appropriately shaped portion 288, and connected to a contact plug 283 by means of a terminal lead 2851 that is enclosed by a ring-shaped glass element 286 and joined to the connector plug 283 through a press-clamped connection 284;

FIG. 5 is the upper portion of the apparatus 1 according to the invention with a sliding stage 11 that is guided by means of track rails 12 and driven by means of a first motor 13 and a spindle drive 14, wherein a second motor 15 is mounted on the sliding stage 11 and coupled to a rotary shaft 16 running parallel to the guide track of the sliding stage 11, and wherein the interior tube 21 of the glass body of FIG. 4 is held by the rotary shaft 16;

FIG. 6 is the lower part of the apparatus 1 with energy radiators 17 and a guide block 40, which is equipped with at least one light gate 53 and contains a hollow cylinder 41 into which the glass body 20 is lowered to the point where it reaches the light gate 53;

FIG. 7 is the lower part of the apparatus 1 after the glass body 20 has been raised by a minimal amount into a range where the ring-shaped glass element 286 is positioned in the upper part of the radiation zone of the energy radiators 17 which will subsequently be activated.

DETAILED DESCRIPTION OF A PREFERRED EMBODIMENT

Figure 1:
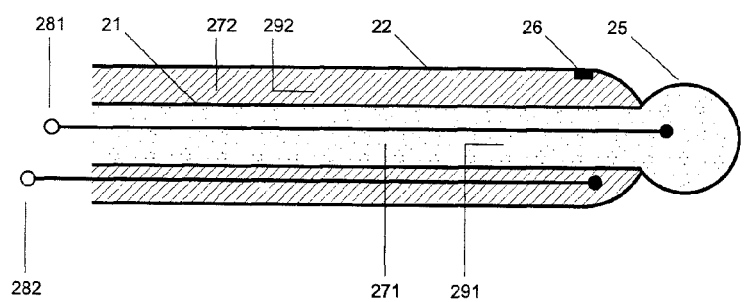
FIG. 1 is a known pH electrode with a lead-off element 281 that is immersed in an inner buffer 271 in a first chamber 291 inside an interior tube 21 which ends in a thin-walled spherically shaped glass membrane 25 and is surrounded by an exterior tube 22.

The following explanation of the inventive apparatus 1 and the inventive method refers to the exemplary embodiments shown in FIGS. 4 to 8. Essential method steps are identified by the letters A through G and are indicated in the drawings by a hand with an extended index finger.

FIG. 1 schematically represents a pH electrode according to the known prior art, with a lead-off element 281 that is immersed in an inner buffer 271 in a first chamber 291 inside an interior tube 21 which ends in a thin-walled spherically shaped glass membrane 25 and is surrounded by an exterior tube 22. The functional principal of this pH electrode has been explained at the outset.

Figure 2A:
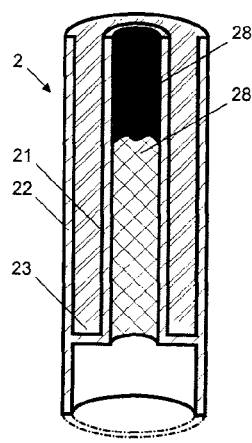
FIG. 2a is an immersion tube 2 of the preferred configuration prior to picking up a gob 24 of molten glass.
Figure 2B:
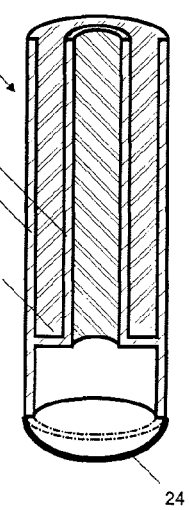
FIG. 2b is the immersion tube 2 of FIG. 2a after picking up the gob 24.

The manufacture of a glass body 20 that is suitable for further processing under the inventive method has been described above with reference to FIGS. 2a to 2c.

Figure 3A:
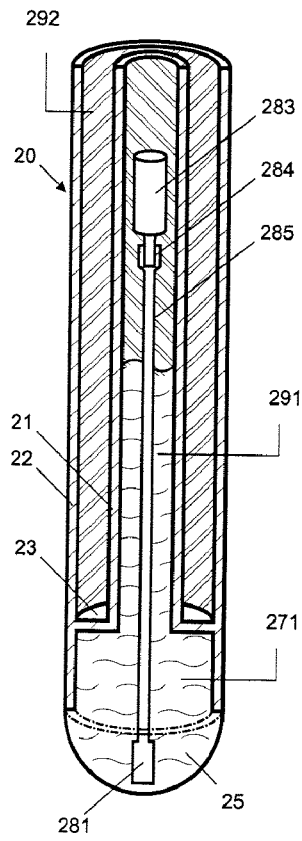
FIG. 3a is the glass body 20 of FIG. 2c, after the chamber 291 has been filled with the inner buffer 271 and the lead-off element 281 has been installed, which is connected to a contact plug 283.
Figure 3B:
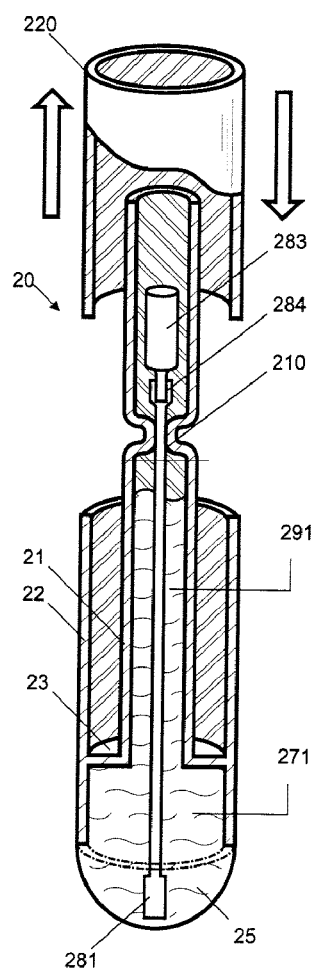
FIG. 3b is the glass body 20 of FIG. 3a after the first chamber 291 has been closed off by fusing the interior tube 21 in accordance with a known method.

A known prior-art method of processing the glass body 20 has been described with reference to FIGS. 3a and 3b, where the first chamber 291 of the glass body is filled with an inner buffer 271 and where a lead-off element 281 is installed which is connected to a plug contact 283. FIG. 3b illustrates the glass body 20 of FIG. 3a after the first chamber 291 has been closed off by fusing the interior tube 21 in accordance with the known prior-art method.

Figure 2C:
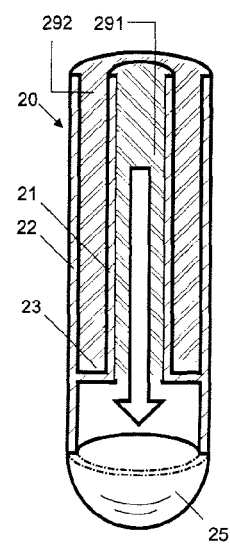
FIG. 2c is the immersion tube 2 of FIG. 2b after it has been made into a glass body 20 with a first chamber 291 which is closed off on one side by a glass membrane 25 that was formed out of the gob 24, and with the second chamber 292 that is delimited by the outside wall of the interior tube 21 and the inside wall of the exterior tube 22.

FIG. 4 represents the glass body 20 of FIG. 2c with a slightly lengthened interior tube 21, through which an inner buffer 271 has been poured into the first chamber 291. A lead-off element 281 has been inserted into the first chamber 291 and centered in the interior tube 21 by a spiral-shaped portion 288 of the connecting lead 2852. The latter consists of silver and silver chloride and is connected to a terminal lead 2851 which in this preferred embodiment is joined to a plug contact by means of a press-clamped connection 284. Within the interior tube 21, the terminal lead 2851 is positioned in the portion 210 that is to be fused.

The terminal lead 2851, which consists of a precious metal (for example platinum), is surrounded by a ring-shaped glass element 286 that is designed to absorb radiation energy. The radiation-absorbing glass element 286 contains metal oxides or metals that are present in monolithic form or in more than one piece, or in particle form, for example iron oxide. The metal oxides are heated by exposure to radiation energy, for example infrared radiation, or by inductive energy-coupling, which causes the glass element 286 to melt. One could also use other materials that can be heated by exposure to radiation energy. As mentioned above, one could also use more than one radiation-absorbing glass element 286, and the latter could also be in powder form. A glass element 286 can be positioned in the vicinity of the terminal lead 2851 or in the vicinity of the connecting lead 2852.

An apparatus for fusing a glass ring by means of infrared radiation is known from U.S. Pat. No. 6,354,901 B1 to Bundo. The fusing of the glass ring serves to close off a passage opening through which an electrode is introduced into a discharge lamp. In this fusion process, the glass ring is set in place at the opening of the discharge lamp and fused, so that the molten material can flow vertically from above into the opening without melting the glass of the discharge lamp itself.

In the processing of glass bodies 20 according to the invention, the glass bodies are brought into the operating range of at least one energy radiator 17 (see FIGS. 6 to 8) in such a way that the glass element 286 can be exposed to the required amount of radiation energy. As described above, it is essential to the inventive method that the fusion process and the forces that act on the parts adjacent to the fusion zone are precisely controlled. This is accomplished advantageously by using the inventive apparatus 1 shown in FIGS. 5 to 8.

FIG. 5 represents the upper part of the inventive apparatus 1, which has a sliding stage 11 guided by means of track rails 12 and driven by a first motor 13 and a drive spindle 14. A second motor 15, which is mounted on the sliding stage 11, has a rotary drive shaft 16 oriented in the downward vertical direction and aligned parallel to the track of the sliding stage 11.

In the illustrated embodiment, the diameter of the rotary drive shaft 16 is equal to the internal diameter of the interior tube 21 of the glass body 20 shown in FIG. 4, so that the interior tube can be slid over the rotary drive shaft 16 in a process step A. Of course, the interior tube 21 could also be gripped and held on its outside surface.

FIGS. 6 and 7 show the lower part of the apparatus 1 with two schematically represented energy radiators 17 and a guide block 40 with at least one light gate 53, all of which are arranged in a housing 10. In a process step B, the sliding stage 11 is lowered until the glass body 20 is inserted far enough into a hollow cylinder 41 (shown in cross-section) which is connected to the guide block 40, so that the glass body interrupts the light gate 53 which is formed by a light source 51 and an optical sensor 52, the latter being connected to a control unit 100 (see FIG. 8).

Figure 8:
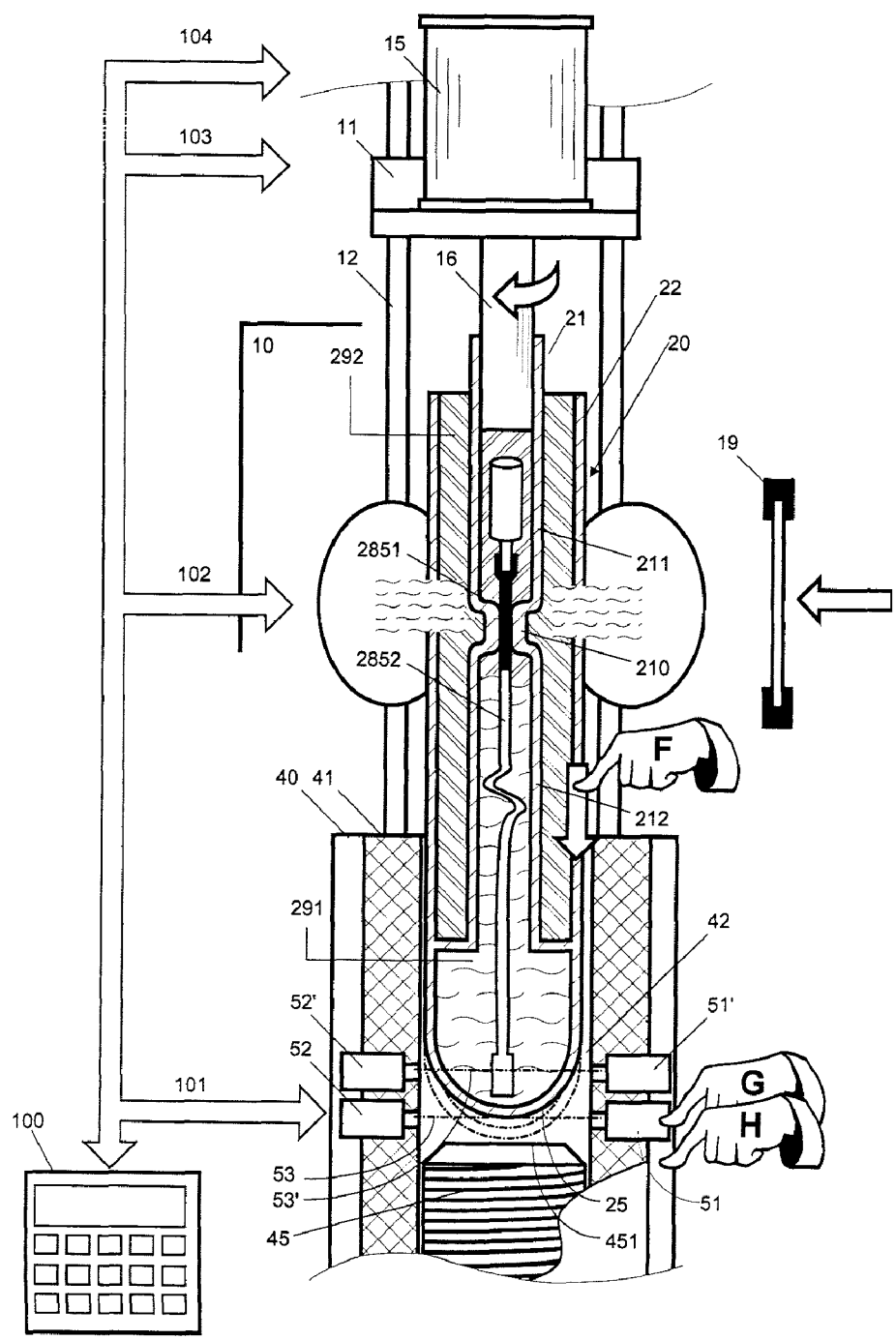
FIG. 8 is the lower part of the apparatus 1 after the ring-shaped glass element 286 and the adjacent portion 210 of the interior tube 21 have been fused together and the lower part 212 together with the exterior tube 22 has slid downwards, thereby interrupting the light gate 53 which serves to switch off the energy radiators 17, with the downward movement being stopped by a screw 45 that is installed in the hollow cylinder from below.

In process step B, the light gate 53 has the function of a reference line which indicates to the control unit 100 that the sliding stage 11, or more specifically the glass body 20, has reached a reference position. This enables the control unit 100 to stop the movement of the sliding stage 11 and to raise the stage by a predetermined distance in a subsequent process step C, so that the glass element 286, which has been set into position in the glass body 20, is in the working range of the energy radiators 17. This process step (C) is made unnecessary, if a second light gate 51', 52', 53' is arranged in an appropriate position, as shown in FIG. 8. In the latter case, the glass body is lowered to the second light gate 51', 52', 53' in process step B, and the method continues subsequently with process step D. The first and/or the second light gate 51, 52, 53, 51', 52', 53' can also be replaced by a non-optical sensor, for example by a capacitive sensor.

In a further process step D (see FIG. 7) which is part of the preferred embodiment of the invention, the second motor 15 is switched on, so that the glass body 20, which is held by the rotary drive shaft 16 and extends into the interior space 42 of the hollow cylinder 41, is set into rotation. In the subsequent process step E, the energy radiators 17 are also switched on, whereby the glass element 286 is heated so that it begins to enter a phase of viscous flow. Because of the centrifugal forces which are caused by the rotary movement, the molten material of the glass element 286 is pulled outward and pressed against the inside wall of the portion 210 of the interior tube 21 that is to be fused, whereby the wall portion 210 is likewise heated, ideally in a uniform manner, which causes the wall portion 210 to melt so that it attaches itself solidly to the terminal element 2851 and forms a tight closure on the first chamber 291.

FIG. 8 illustrates the glass tube 20 after the glass element 286 and the surrounding portion 210 of the interior tube 21 have been fused together, and it also shows the viscous-flow phase of the molten material (process step F). The flow process causes the heated interior tube portion 210 to collapse. As the lower part 212 of the interior tube 21 and the rest of the immersion tube 20 are only loosely held through the viscous connection, they will descend vertically. In other words, the upper part 211 of the interior tube 21 remains in a fixed hold on the rotary drive shaft 16, while the lower part 212 with the rest of the glass body 20 moves downward until the glass membrane 25 that closes off the first chamber 291 meets a limit stop (process step H) that is formed by a screw 45 installed in the hollow cylinder 41 from below. Having been adjusted to an appropriate height setting, the screw 45 has the effect that the interior tube collapses only along a segment of desired length and is not torn in two.

It shall be mentioned here that collapsing of the interior tube 21 during melting is not to be regarded as a precondition necessary for the production of a hermetical closure of the first chamber 291 and it is therefore of less importance for its tightness. For that purpose the fusion-melting of the glass element 286 and the fused portion 210 of the wall of the interior tube 21 is relevant. The collapse of the tube wall is a consequence of downward movement of the lower part 212 of the interior tube 21.

To make the apparatus adaptable for the production of immersion tubes 20 of different dimensions, the hollow cylinder 41 and the screw 45 that is seated in the hollow cylinder are preferably adjustable within the required range. For example, the hollow cylinder 41 can be mounted on a second, lower sliding stage that is likewise movable along the axis x indicated in FIG. 6, analogous to the first, upper sliding stage 11. In the illustrated embodiments of the apparatus 1, the axis x runs preferably in the vertical direction, but embodiments with an inclined axis x are also conceivable.

Before contacting the end surface 451 of the screw 45, the glass body 20 traverses the light gate 53 (process step G), whereby the control unit 100 detects the condition of viscous flow. At this point, or possibly with a programmed delay, the energy radiators 17 can be switched off, so that excessive heating of the glass body 20 is avoided.

FIG. 8 further shows the control unit 100 which has a keyboard and a display and communicates through electrical connections 101 to 104 with the two motors 13 and 15, with the energy radiator, and with the light gates 51, 52, 53; 51', 52', 53'. The housing 10 is indicated schematically. It has a door with a window of protective glass, for example a filter panel, through which the fusion process can be observed and controlled.

The inventive apparatus 1 and the inventive method have been described and represented through preferred embodiments. However, the concepts of the invention as taught herein will enable a person of ordinary skill in the art to realize further variations of the inventive concept. The apparatus 1 shown herein has been adapted for the manufacture of the illustrated glass bodies. However, with a knowledge of the essential functional principles, the inventive apparatus 1 can also be adapted to the manufacture of other glass bodies. This may in some cases involve that steps or movements are performed in reverse order or direction. Furthermore, the level of automation implemented in the apparatus 1 can be selected according to what the application requires.

The glass bodies illustrated and described are designed for installation in chemical sensors or measuring probes. As is self-evident, the inventive method also lends itself to the manufacture of any other multi-walled glass bodies.

Of course, the method according to the invention can also be used to manufacture multi-walled glass bodies in which two or more chambers have to be closed off or where two or more fused connections between walls have to be made. The task is accomplished in this case by inserting two or more appropriately shaped energy-absorbing glass elements in the glass body.

Instead of a connector lead 2852 or a lead-off element 281 and the terminal lead 2851 which does not melt in the fusion process, it is also possible to use equivalent metallic conductors 2851', 2852' which are applied to the inside surface of the interior tube 21 in one or more layers.

What is claimed is:

1. A method for closing an interior tube of a multi-walled glass body to form a first chamber, while the interior tube is surrounded by an exterior tube, at least at the closure, the method comprising the steps of:
    inserting, in the interior tube in the vicinity of the closure, at least one energy-absorbing glass element, in solid or in powder form, the glass element and containing metal or metal oxide particles that absorb radiative energy more readily than the glass in the multi-walled glass body;
    fusion-melting the energy-absorbing glass element to the interior tube at the closure, using radiative energy generated by at least one energy radiator with heat generated in the metal or metal oxide particles softening the glass in the glass element and in the adjoining interior tube, resulting in a soft melting zone being displaced relative to the exterior tube; and
    sensing the displacement with a sensor, which signals a control unit to control the fusion-melting step.

2. The method of claim 1, further comprising the step of:
    providing at least one metallic conductor, in the form of either a wire or of a surface layer adhering to the interior tube.

3. The method of claim 2, further comprising the step of:
    inserting the at least one energy-absorbing glass element and a terminal lead, which does not melt during the fusion-melting step, into the interior tube after the interior tube has been closed off at one end,
    wherein the terminal lead passes through the portion to be fused and connects a lead-off element that is immersed in a medium occupying the first chamber with a connector part or contact plug arranged outside of the first chamber.

4. The method of claim 1, further comprising the step of:
    inserting the at least one energy-absorbing glass element and a terminal lead, which does not melt during the fusion-melting step, into the interior tube after the interior tube has been closed off at one end,
    wherein the terminal lead passes through the portion to be fused and connects a lead-off element that is immersed in a medium occupying the first chamber with a connector part or contact plug arranged outside of the first chamber.

5. The method of claim 3, wherein:
the at least one energy-absorbing glass element is heated by exposure to radiation energy, through infrared radiation or through inductive coupling.

6. The method of claim 1, wherein:
the at least one energy-absorbing glass element is heated by exposure to radiation energy, through infrared radiation or through inductive coupling.

7. The method of claim 3, further comprising the steps of:
providing a sliding stage which is guided by track rails and driven by a motor;
attaching the glass body to the sliding stage in a preferably vertically aligned position of a longitudinal axis of the glass body, and
moving the sliding stage subsequently into a range where the radiative energy can have an effect on the energy-absorbing glass element.

8. The method of claim 1, further comprising the steps of:
providing a sliding stage which is guided by track rails and driven by a motor;
attaching the glass body to the sliding stage in a preferably vertically aligned position of a longitudinal axis of the glass body, and
moving the sliding stage subsequently into a range where the radiative energy can have an effect on the energy-absorbing glass element.

9. The method of claim 7, further comprising the step of:
attaching the interior tube to the sliding stage so that, after the radiative energy has been applied and after the energy-absorbing glass element and the adjoining portion of the interior tube have been fused, a part of the glass body that is held only by the portion of the interior tube being fused is pulled downward by its own weight until the sensor detects the downward movement and sends the signal to the control unit, which switches the energy radiator off.

10. The method of claim 9, further comprising the steps of:
lowering the glass body to the level of the sensor prior to the fusion-melting step; and
raising the glass body subsequently into a range where the radiative energy can have an effect on the energy-absorbing glass element.

11. The method of claim 9, further comprising at least one of the steps of:
guiding the glass body in the axial direction by a guide block which can be movably supported; and
providing an end stop so that the glass body meets the end stop subsequent to traversing the sensor.

12. The method of claim 7, wherein:
the interior tube is connected to a rotary drive shaft of a motor mounted on the sliding stage, the rotary drive shaft being aligned parallel to the direction of movement of the sliding stage, and
the motor is set in motion before and during the heating of the glass element.

* * * * *